United States Patent
Eto et al.

(10) Patent No.: US 10,941,382 B2
(45) Date of Patent: Mar. 9, 2021

(54) PLATELET PRODUCTION PROMOTER AND METHOD OF PRODUCING PLATELETS USING SAME

(71) Applicants: Kyoto University, Kyoto (JP); Megakaryon Corporation, Kyoto (JP)

(72) Inventors: Koji Eto, Kyoto (JP); Hideya Seo, Kyoto (JP); Akira Ota, Kyoto (JP); Yukitaka Ito, Kyoto (JP); Yasuko Hazama, Kyoto (JP)

(73) Assignees: Kyoto University, Kyoto (JP); Megakaryon Corporation, Kyoto (JP)

( * ) Notice: Subject to any disclaimer, the term of this patent is extended or adjusted under 35 U.S.C. 154(b) by 202 days.

(21) Appl. No.: 16/071,598

(22) PCT Filed: Jan. 30, 2017

(86) PCT No.: PCT/JP2017/003191
§ 371 (c)(1),
(2) Date: Jul. 20, 2018

(87) PCT Pub. No.: WO2017/131230
PCT Pub. Date: Aug. 3, 2017

(65) Prior Publication Data
US 2019/0032015 A1    Jan. 31, 2019

(30) Foreign Application Priority Data

Jan. 29, 2016   (JP) .............................. JP2016-016677

(51) Int. Cl.
| | |
|---|---|
| *C12N 5/078* | (2010.01) |
| *A61P 7/04* | (2006.01) |
| *A61K 31/444* | (2006.01) |
| *A61K 31/381* | (2006.01) |
| *C12N 15/09* | (2006.01) |
| *A61K 35/19* | (2015.01) |

(52) U.S. Cl.
CPC .......... *C12N 5/0644* (2013.01); *A61K 31/381* (2013.01); *A61K 31/444* (2013.01); *A61P 7/04* (2018.01); *C12N 15/09* (2013.01); *A61K 35/19* (2013.01); *C12N 2501/26* (2013.01); *C12N 2501/415* (2013.01); *C12N 2501/727* (2013.01); *C12N 2501/999* (2013.01); *C12N 2506/11* (2013.01); *C12N 2506/45* (2013.01)

(58) Field of Classification Search
CPC ............ C12N 5/0644; C12N 2501/999; C12N 2506/11; C12N 2506/45
See application file for complete search history.

(56) References Cited

U.S. PATENT DOCUMENTS

2011/0172398 A1 * 7/2011 Borges .................... A61P 43/00
530/387.3
2018/0271849 A1 * 9/2018 Ge ..................... A61K 31/4166

FOREIGN PATENT DOCUMENTS

| JP | 2005-187435 A | 7/2005 |
| WO | 2014138485 A1 | 9/2014 |
| WO | 2014168255 A1 | 10/2014 |
| WO | 2015174443 A1 | 11/2015 |

OTHER PUBLICATIONS

Takayama, et al., "Generation of functional platelets from human embryonic stem cells in vitro via ES-sacs, VEGF-promoted structures . . . hematopoietic progenitors", Jun. 1, 2008, pp. 5298-5306, vol. 111, No. 11, Publisher: Blood.
Koo et al., "Porcupine inhibitor suppresses paracrine Wnt-driven growth of Rnf43;Znrf3-mutant neoplasia", Jun. 16, 2015, pp. 7548-7550, vol. 112, No. 24, Publisher PNAS USA.
Patch et al., "Identification of 2-acylaminothiophene-3-carboxamides as potent inhibitors of FLT3", Jun. 15, 2006, pp. 3282-3286, vol. 16, No. 12, Publisher: Bioorg Med Chem Let.
Office Action received in JP2017563891, dated Jan. 20, 2021.
Katoh & Katoh, "WNT signaling pathway and stem cell signaling network", Jul. 15, 2007, pp. 4042-4045, vol. 13, No. 14, Publisher Clin Cancer Res.
Shurin et al, "FLT3: receptor and ligand Biology and potential clinical application", 1998, pp. 3748, vol. 9, No. 1, Publisher: Cytokine Growth Factor Rev.

* cited by examiner

*Primary Examiner* — Marcia S Noble
(74) *Attorney, Agent, or Firm* — Suzannah K. Sundby, Esq.; Canady + Lortz LLP (57) ABSTRACT

The present invention provides: a platelet production promoter that contains one or more substances selected from the group consisting of Wnt inhibitors and FMS-like tyrosine kinase (FLT) inhibitors; and a platelet production method that uses this platelet production promoter.

15 Claims, 3 Drawing Sheets

Specification includes a Sequence Listing.

PLATELET PRODUCTION PROMOTER AND METHOD OF PRODUCING PLATELETS USING SAME

REFERENCE TO A SEQUENCE LISTING SUBMITTED VIA EFS-WEB

The content of the ASCII text file of the sequence listing named "20180729_101621_006US1_seq", which was filed in PCT/JP2017/003191 on Jan. 30, 2017, downloaded from the WIPO database, is 1.67 kb in size with a created date of Jul. 17, 2018, and electronically submitted via EFS-Web herewith the application, is incorporated herein by reference in its entirety.

TECHNICAL FIELD

The present invention broadly relates to a platelet production promoter and a platelet production method.

BACKGROUND ART

Blood cells are required for the treatment of blood-related diseases and for surgical operations. Among blood cells, platelets, which are cells required for blood coagulation (hemostasis), proplatelets, and megakaryocyte cells, which are cells that produce platelets, are cells where the need is particularly high. Leukemia treatments, bone marrow transplantation, and anticancer therapies create great demand for platelets in particular, and the requirement for a stable platelet supply is thus acute.

To date, methods in which various types of stem cells are differentiated to obtain megakaryocyte cells and these are cultured to release platelets, have been developed as in vitro platelet production methods. Due to the creation of iPS cells, greater attention has been directed in recent years to the usefulness of pluripotent stem cells as an important source of cell therapies in regenerative medicine. To date, for example, Takayama et al. have succeeded in inducing the differentiation of human ES cells into megakaryocyte cells and platelets (Non-Patent Document 1). However, it has also been seen that the platelets obtained in vitro to date have not had their native functionalities to a satisfactory degree, i.e., they have not had a satisfactory blood coagulation performance.

The acquisition of adequately functional platelets without using feeder cells has not been easy in conventional in vitro platelet production methods. However, cells originating from non-human species are also frequently used for the feeder cells, and a method that does not use feeder cells is desired for the production of platelets that are supplied to humans.

In one example of methods proposed to date for the in vitro production of platelets from hematopoietic progenitor cells, a method has been proposed in which megakaryocyte cells are cultured in the presence of TPO and an aryl hydrocarbon receptor (AhR) antagonist (Patent Document 1).

CITATION LIST

Patent Document

Patent Document 1: WO 2014/138485

Non-Patent Document

Non-Patent Document 1: Takayama N. et al., Blood, 111, pp. 5298-5306, 2008.

SUMMARY

Technical Problem

The problem for the present invention is to provide a novel platelet production promoter and a platelet production method that uses this platelet production promoter.

Solution to Problem

As a result of extensive investigations in order to solve this problem, the present inventors discovered that a Wnt signal transduction inhibitor and an FMS-like tyrosine kinase (FLT) inhibitor have a platelet production promoting-effect that is the same as or greater than that of AhR antagonists. The present invention was achieved based on this discovery.

That is, the present invention provides the following inventions.

(1) A platelet production promoter containing one or more substances selected from the group consisting of Wnt inhibitors and FLT inhibitors.

(2) The platelet production promoter according to (1), wherein the Wnt inhibitor is C59.

(3) The platelet production promoter according to (1), wherein the FLT inhibitor is an FLT3 inhibitor.

(4) The platelet production promoter according to any one of (1) to (3), further containing a ROCK inhibitor.

(5) A method of producing platelets, the method including a step for bringing megakaryocyte cells and/or progenitor cells thereof into contact with one or more substances selected from the group consisting of Wnt inhibitors and FLT inhibitors.

(6) The method according to (5), wherein the Wnt inhibitor is C59.

(7) The method according to (5), wherein the FLT inhibitor is an FLT3 inhibitor.

(8) The method according to any one of (5) to (7), further including a step for bringing the megakaryocyte cells or progenitor cells thereof into contact with a ROCK inhibitor.

(9) The method according to any one of (5) to (8), wherein the megakaryocyte cells are immortalized megakaryocyte cells.

(10) The method according to (9), wherein the pluripotent stem cells are iPS cells.

(11) The method according to (10), wherein the iPS cells are of human origin.

Advantageous Effects of Invention

A platelet production-promoting effect that is the same as or greater than that of AhR antagonists is obtained using the platelet production promoter according to the present invention. In addition, even without the use of feeder cells, the platelet production promoter according to the present invention can achieve a platelet production-promoting effect that matches the use of feeder cells in the absence of a platelet production promoter. That is, the platelet production promoter-effect provided by the present invention is considered to have the effect of replacing the role of feeder cells. As a consequence, the use of the platelet production promoter according to the present invention enables megakaryocyte cells to be cultured in a vertical large-scale cultivation apparatus and thus supports the efficient mass production of platelets for clinical applications.

DESCRIPTION OF EMBODIMENTS (The Platelet Production Promoter)

The platelet production promoter according to the present invention contains, as its effective component, one or more substances selected from the group consisting of Wnt inhibitors and FLT inhibitors. Wnts are secreted glycoproteins with molecular weights of approximately 40,000. As used in this Description, "Wnt inhibitor" denotes any substance that inhibits signal transduction that is activated by the action of Wnt protein on the cell (referred to in the following simply as "Wnt signal transduction"), for example, any substance that inhibits the expression or function (activity) of Wnt protein. The targets for Wnt inhibitors can be exemplified by β-catenin, PORCN, casein kinase 1, tankyrase, and glycogen synthase kinase 3, but this is not intended as limiting. The following compounds can be used as Wnt inhibitors.

β-catenin:
Calphostin C
Cardionogen 1
CCT 031374 hydrobromide
FH 535
ICG 001
iCRT 14
IWP 4
endo-IWR 1
exo-IWR 1
JW 67
JW 74 New product
PNU 74654
TAK 715
WAY 316606 hydrochloride
XAV 939

PORCN:
IWP 12
IWP 2
IWP L6
Wnt-C59
 Casein Kinase 1:
CKI 7 dihydrochloride
(R)-CR8
D 4476
(R)-DRF053 dihydrochloride
LH 846
PF 4800567 hydrochloride
PF 670462
TA 01
TA 02
TAK 715
 Tankyrase:
JW 55
MN 64
TC-E 5001
WIKI4
XAV 939
 Glycogen Synthase Kinase 3:
3F8
A 1070722
AR-A 014418
BIO
BIO-acetoxime
CHIR 99021
10Z-Hymenialdisine
Indirubin-3'-oxime
Kenpaullone
L803
L803-mts
MeBIO
NSC 693868
SB 216763
SB 415286
TC-G 24
TCS 2002
TCS 21311
TWS 119

Nonlimiting examples of Wnt inhibitors are compounds that inhibit any

Wnt signal transduction pathway, for example, C59 (4-(2-methyl-4-pyridinyl)-N-[4-(3-pyridinyl)phenyl]benzeneacetamide) and its analogs, e.g., IWP 12, IWP 2, IWP L6, and so forth, and their salts and derivatives; also, anti-Wnt antibodies and their antibody fragments, antisense oligonucleotides, ribozymes, and molecules that induce RNA interference ("RNAi" below). The FLT inhibitor is TCS-359 in a preferred embodiment.

FLT1 to FLT4 are known as members of FLT, which is an FMS-like tyrosine kinase. As used in this Description, "FLT inhibitor" refers to any substance that inhibits the expression or function (activity) of an FMS-like tyrosine kinase (FLT) and preferably FLT3 in particular. Nonlimiting examples of FLT inhibitors are TCS-359 (2-[(3,4-dimethoxybenzoyl)amino]-4,5,6,7-tetrahydrobenzo[b]thiophene-3-carboxamide) and its analogs and their salts and derivatives; also anti-FLT antibodies and their antibody fragments, antisense oligonucleotides, ribozymes, and molecules that induce RNA interference (RNAi). The FLT inhibitor is preferably an FLT3 inhibitor and is particularly preferably TCS-359.

Insofar as the desired effects are achieved, the platelet production promoter may contain, as its effective component, one or more inhibitors as described above. The concentration of the inhibitor in the platelet production promoter is not particularly limited and can be established as appropriate by the individual skilled in the art. For example, when C59 is used as the Wnt inhibitor, 1.0 nM to 1.0 mM, or 10 nM to 0.1 mM, or 100 nM to 0.01 mM can be used, and, when TCS-359 is used as the FLT3 inhibitor, 1.0 nM to 1.0 mM, 10 nM to 0.1 mM, or 100 nM to 0.01 mM can be used; however, the amount may be outside these ranges insofar as the desired effects are achieved.

In this Description, the term "protein expression" is used in the sense of including both transcription and translation, while "inhibition of expression" denotes the complete or partial inhibition of expression at the level of transcription or at the level of translation.

The step for inhibiting the expression or function of Wnt or FLT can be carried out using a known method or a method based thereon.

A dominant negative method may be used as the method for inhibiting the function of Wnt or FLT. In the dominant negative method, a Wnt protein and/or FLT protein with an activity reduced or extinguished by the introduction of mutation is expressed in large amounts in the cell to provide an overwhelmingly high ratio within the cell of the corresponding inactive protein relative to the normal Wnt protein and/or FLT protein, thus yielding a cell that exhibits a behavior in which the function of the Wnt protein and/or FLT protein is not obtained.

An anti-Wnt antibody or an anti-FLT antibody may be used as a method for inhibiting the functionality of Wnt protein and/or FLT protein. The anti-Wnt antibody or anti-FLT antibody used may be an antibody produced by a known method or may be a commercial antibody, and may be any antibody that provides the effects of the present invention through inhibition of the functionality of Wnt protein and/or FLT protein.

The use of miRNA that inhibits the expression of an Wnt gene or FLT gene is an example of a method for inhibiting the expression of Wnt protein and/or FLT protein. The miRNA may be miRNA that acts directly on the Wnt gene or FLT gene or that acts thereon indirectly.

"miRNA" is short-chain (20 to 25 bases) noncoding RNA present intracellularly, that is involved in the regulation of gene expression via degradation of mRNA or inhibition of translation from mRNA to protein. This miRNA is transcribed as a single-stranded pri-miRNA that can assume a hairpin loop structure containing the miRNA and its complementary chain; a portion of this is cleaved in the nucleus by the enzyme known as Drosha to provide a pre-miRNA; and this is transported out of the nucleus and is then further cleaved by Dicer to provide the functional miRNA. Accordingly, the let-7 and miR181a used in the present invention may be the single-stranded pri-miRNA or may be in the form of the double-stranded pre-miRNA.

An antisense method, ribozyme method, or RNAi method may be used as the method for inhibiting the expression of the Wnt gene or FLT gene.

In the antisense method, gene expression is inhibited using a single-stranded nucleic acid that has a length generally of 10 bases to 100 bases and preferably 15 bases to 30 bases and that has a base sequence complementary to the target gene (basically to the mRNA that is the transcript). The antisense nucleic acid is introduced into the cell, and gene expression is then inhibited by hybridization with the target gene. As long as the expression-inhibiting effect on the target gene is obtained, the antisense nucleic acid may not be completely complementary to the target gene. Antisense nucleic acid can be designed as appropriate by the individual skilled in the art using, for example, known software. The antisense nucleic acid may be DNA, RNA, or a DNA-RNA chimera and may be modified.

A ribozyme is a nucleic acid molecule that can catalytically hydrolyze a target RNA, and is constructed of an antisense region having a sequence complementary to the target RNA and a catalytic core region responsible for the cleavage reaction. Ribozymes can be designed as appropriate by the individual skilled in the art using known methods. While ribozymes are typically RNA molecules, a DNA-RNA chimeric molecule may also be used.

The RNAi method is a sequence-specific gene expression inhibition mechanism that is induced by a double-stranded nucleic acid. The target specificity is very high, and the safety is also high because this method utilizes a gene expression inhibition mechanism that is natively present in the organism.

siRNA is an example of a double-stranded nucleic acid having an RNAi effect. When used in mammalian cells, siRNA is a double-stranded RNA generally of about 19 to 30 bases and preferably about 21 bases to 25 bases. Double-stranded nucleic acid having an RNAi effect generally has, on the one side, a base sequence that is complementary to a portion of the target nucleic acid, and, on the other side, a sequence complementary to this. An siRNA that inhibits the expression of Wnt or FLT can be designed as appropriate by the individual skilled in the art using, for example, known software. The target sequence used in the examples given below is an example of the one side of the double-stranded nucleic acid sequence. siRNA that inhibits the expression of Wnt or FLT may act directly on the Wnt gene or FLT gene (i.e., contains a sequence complementary to a portion of the Wnt gene or FLT gene) or may act indirectly (i.e., inhibits the expression of the Wnt gene or FLT gene as a result of inhibition of the expression of a gene other than the Wnt gene or FLT gene).

Expression within a cell can be brought about by the introduction into the cell of a vector (for example, a lentivirus vector) that contains nucleic acid encoding the particular siRNA, antisense nucleic acid, or ribozyme, but, in addition to this, introduction into the cell in the form of RNA may also be performed. In the case of introduction in RNA form, introduction into a cell may be carried out using a known procedure, e.g., lipofection, microinjection, and so forth. In order to inhibit degradation of the RNA, use may be made of RNA that incorporates 5-methylcytidine or pseudouridine (TriLink Biotechnologies) (Warren L., (2010) Cell Stem Cell, 7:618-630) or a DNA-RNA chimera that incorporates DNA. For both uridine and cytidine, the position of the modified base may independently be for all or a portion, and when it is for a portion, it may be a random position in any proportion. The following may be used for the vector containing the siRNA-encoding nucleic acid: a vector containing DNA that encodes each of the two strands, or a vector containing DNA encoding single-stranded nucleic acid that can form double-stranded nucleic acid connected through a loop. In the case of siRNA, the single-stranded RNA provided by transcription within the cell may be designed such that its complementary region hybridizes within the cell with the assumption of a hairpin structure. Such RNA is referred to as short hairpin RNA (shRNA). Upon transfer to the cytoplasm, the loop region of the shRNA is digested by an enzyme (Dicer) to yield the siRNA, thereby expressing the RNAi effect.

When, in this Description, the inhibition of protein expression is said to be "brought about by siRNA" or "brought about by miRNA", this means that expression is ultimately inhibited by siRNA or miRNA; the siRNA, shRNA, or miRNA may be delivered into the cell in the form of RNA or a vector containing nucleic acid encoding the siRNA, shRNA, or miRNA may be delivered into the cell.

When siRNA or shRNA for a Wnt gene or an FLT gene is introduced using, for example, a vector, the expression of this RNA may be controlled using a drug-responsive promoter. Such a vector that enables drug-responsive control of the RNA can be acquired from, for example, Takara Bio Inc. Here, the introduction of the RNA denotes effecting contact with the corresponding drug and thereby inducing expression of the RNA within the cell.

The platelet production promoter according to the present invention can increase the amount of platelet production from megakaryocyte cells. While not intended as a limitation, an inhibitor that brings about a significant increase in the number of platelets relative to the negative control, for example, an increase of at least 10%, at least 20%, at least 50%, or at least 100 or 200%, is preferred as the effective component of the platelet production promoter according to the present invention. The platelet production promoter according to the present invention may be used by itself or may be used in combination with another, already known platelet production promoter substance. There are no particular limitations on the timing of the addition of the platelet production promoter insofar as the desired effects are achieved. For example, addition of the platelet production promoter to the megakaryocyte cells prior to multinucleation or after multinucleation, and particularly to the megakaryocyte cells during platelet production, may be contemplated.

In another embodiment, the platelet production promoter according to the present invention may additionally contain an Aryl hydrocarbon receptor (AhR) antagonist as an effective component. As used in this Description, an "aryl hydrocarbon receptor (AhR)" is a transcription factor belonging to the Per/ARNT/SIM (PAS) family. AhR is inactive when not bound to a ligand, but translocates to the nucleus when bound with an aromatic hydrocarbon compound ligand. In the nucleus, it forms a heterodimer with a molecule known as AhR nuclear translocator (ARNT), which activates transcription by binding to a xenobiotic response element (XRE) on the DNA.

Nonlimiting examples of AhR antagonists that may be used by the present invention are as follows:
4-(2-(2-(benzo[b]thiophen-3-yl)-9-isopropyl-9H-purin-6-ylamino)ethyl)phenol (SR1);
α-naphthoflavone;
1,4-dihydroxyanthraquinone;
1,5-dihydroxyanthraquinone;
1,8-dihydroxyanthraquinone;
galangin;
resveratrol;
2-methyl-2H-pyrazole-3-carboxylic acid (2-methyl-4-o-tolylazophenyl)amide (CH-223191);
N-[2-(3H-indol-3-yl)ethyl]-9-isopropyl-2-(5-methyl-3-pyridyl)purin-6-amine (GNF351);
2-(29-amino-39-methoxyphenyl)oxanaphthalen-4-one (PD98059);
(Z)-3-[(2,4-dimethylpyrrol-5-yl)methylidenyl]-2-indolinone (TSU-16);
2-(29-amino-39-methoxyphenyl)oxanaphthalen-4-one (PD98059);
6,2',4'-trimethoxyflavone (TMF); and
3',4'-dimethoxyflavone (DMF).

The compounds given as AhR antagonists in WO 2012/015914 may also be used.

There are no particular limitations on the concentration of the AhR antagonist in the platelet production promoter, and this can be established as appropriate by the individual skilled in the art. For example, the functionality of the obtained platelets can be further enhanced in the range of at least 200 nM to less than 1000 mM when SR1 is used; at least 0.2 µM to less than 4 µM when CH223191 is used; at least 20 nM to less than 300 nM when GNF351 is used; at least 2.5 µM to less than 40 µM when TMF is used; and at least 2.5 µM to less than 40 µM when DMF is used. However, the amount may be outside these ranges as long as the desired effects are achieved.

In another embodiment, the platelet production promoter according to the present invention may also contain a ROCK inhibitor. The combination of a Wnt inhibitor and/or FLT inhibitor with a ROCK inhibitor results in an increase in the number of platelets produced and also in a synergetic increase in the functionality of the obtained platelets. The Wnt inhibitor and/or FLT inhibitor and the ROCK inhibitor may be present in the platelet production promoter according to the present invention, or either or both may be used separately from the platelet production promoter. In this Description, "ROCK inhibitor" denotes an antagonist for Rho-binding kinase (Rho-associated coiled-coil forming kinase; ROCK). ROCK inhibitors can be exemplified by Y27632, Y39983, fasudil hydrochloride, ripasudil, SLX-2119, RKI-1447, azaindolel, SR-3677, Staurosporine, H1152 dihydrochloride, AR-12286, and INS-117548, but there is no limitation to the preceding.

When immortalized megakaryocyte cells are produced by the overexpression of an oncogene, polycomb gene, and apoptosis suppression gene in cells less differentiated than megakaryocytes followed by the termination of the overexpression and the development of multinucleation of the immortalized megakaryocyte cells, preferably the ROCK inhibitor is added to the culture medium after termination of the overexpression.

(The Platelet Production Method)

The platelet production method according to the present invention contains a step for bringing megakaryocyte cells and/or progenitor cells thereof into contact with the platelet production promoter. Contact between the platelet production promoter and cells can be carried out in a culture medium. In this Description, "megakaryocyte cells" are characteristically the largest cells present in the bone marrow in an organism and characteristically release platelets. They are also characterized by being positive for the CD41a, CD42a, and CD42b cell surface markers, and may also additionally express a marker selected from the group consisting of CD9, CD61, CD62p, CD42c, CD42d, CD49f, CD51, CD110, CD123, CD131, and CD203c. A "megakaryocyte cell", when multinucleated (polyploidization), has 16× to 32× genomes relative to that in an ordinary cell, and in this Description the term "megakaryocyte cells" by itself includes, insofar as the characteristic features indicated above are present, both multinucleated megakaryocyte cells and pre-multinucleated megakaryocyte cells. "Pre-multinucleated megakaryocyte cells" is also synonymous with "immature megakaryocyte cells" and "growth-phase megakaryocyte cells".

The megakaryocyte cells can be obtained by various known methods. A nonlimiting example of a megakaryocyte cell production method is the method described in WO 2011/034073. Using this method, immortalized megakaryocyte cells that can propagate indefinitely can be obtained by the overexpression of an oncogene and a polycomb gene in a "cell less differentiated than a megakaryocyte cell". In addition, immortalized megakaryocyte cells can also be obtained according to the method described in WO 2012/157586 by inducing the overexpression of an apoptosis suppression gene in a "cell less differentiated than a megakaryocyte cell", i.e., a megakaryocyte progenitor cell (also referred to in this Description simply as a "progenitor cell"). By terminating the overexpression of gene, these immortalized megakaryocyte cells undergo the development of multinucleation and release platelets.

A combination of the methods described in the aforementioned documents may be used to obtain the megakaryocyte cells. In this case, overexpression of an oncogene, overexpression of a polycomb gene, and overexpression of an apoptosis suppression gene may be carried out simultaneously or sequentially. For example, multinucleated megakaryocyte cells may be obtained by bringing about the overexpression of an oncogene and polycomb gene; inhibiting this overexpression; then bringing about the overexpression of an apoptosis suppression gene; and inhibiting this overexpression. In addition, multinucleated megakaryocyte cells may also be obtained by bringing about overexpression of the oncogene, overexpression of the polycomb gene, and overexpression of the apoptosis suppression gene all at the same time and then terminating these overexpressions at the same time. Multinucleated megakaryocyte cells may also be obtained by first inducing overexpression of the oncogene and polycomb gene and then inducing overexpression of the apoptosis suppression gene and terminating these overexpressions at the same time.

In this Description, a "cell less differentiated than a megakaryocyte cell" and a "megakaryocyte progenitor cell" denote a cell that has the capacity to differentiate into a megakaryocyte and that resides in various stages of differentiation from a hematopoietic stem cell lineage to a megakaryocyte cell. Nonlimiting examples of cells less differentiated than megakaryocytes are hematopoietic stem cells, hematopoietic progenitor cells, CD34-positive cells, and megakaryocyteerythroid progenitor cells (MEP). These cells may be obtained by isolation from the bone marrow, umbilical cord blood, or peripheral blood, or may be obtained by inducing differentiation from pluripotent stem cells, e.g., ES cells, iPS cells, and so forth, which are even less differentiated cells.

In this Description, "oncogene" refers to a gene that induces the malignant transformation of a cell within an organism, and examples are MYC family genes (for example, c-MYC, N-MYC, L-MYC), SRC family genes, RAS family genes, RAF family genes, and protein kinase family genes such as c-Kit, PDGFR, and Abl.

In this Description, a "polycomb gene" is known as a gene that functions to circumvent cell senescence by negatively regulating the CDKN2a (INK4a/ARF) gene (Ogura et al., Saisei Igaku [Regenerative Medicine], Vol. 6, No. 4, pp. 26-32; Jesus Gill et al., Nature Reviews Molecular Cell Biology, Vol. 7, pp. 667-677, 2006; Proc. Natl. Acad. Sci. USA, Vol. 100, pp. 211-216, 2003). Nonlimiting examples of polycomb genes are BMI1, Mel18, Ring1a/b, Phc1/2/3, Cbx2/4/6/7/8, Ezh2, Eed, Suz12, HADC, and Dnmt1/3a/3b.

In this Description, "apoptosis suppression gene" refers to a gene that has the function of suppressing the apoptosis of a cell, and can be exemplified by the BCL2 gene, BCL-xL gene, Survivin gene, and MCL1 gene.

Overexpression of genes and termination of the overexpression can be performed by the methods described in WO 2011/034073, WO 2012/157586, WO 2014/123242, and Nakamura S. et al., Cell Stem Cell, 14, 535-548, 2014, and by other known methods and by methods based on the preceding.

As may be understood from the examples, from the standpoint of being effective in the maturation process, i.e., the multinucleation and enlargement of the megakaryocyte cells, the inhibition of the expression or function of Wnt protein and/or FLT protein Wnt protein and/or FLT protein may be carried out in the pre-multinucleated megakaryocyte cells, while from the standpoint of carrying out further multinucleation in the multinucleated megakaryocyte cells, the inhibition of the expression or function of Wnt protein and/or FLT protein Wnt protein and/or FLT protein may be carried out in the multinucleated megakaryocyte cells. The inhibition of the expression or function of Wnt protein and/or FLT protein Wnt protein and/or FLT protein is preferably also carried out in the step for producing platelets from the megakaryocyte cells because this promotes multinucleation and enlargement of the megakaryocyte cells and provides a substantial increase in the number of platelets produced per 1 cell.

When immortalized megakaryocyte cells are produced by the overexpression of an oncogene, polycomb gene, and apoptosis suppression gene in cells less differentiated than megakaryocyte cells followed by the termination of the overexpression and the development of multinucleation of the immortalized megakaryocyte cells, the initiation of the inhibition of the expression or function of Wnt protein and/or FLT protein Wnt protein and/or FLT protein may be prior to or after the termination of the overexpression of these genes without particular limitation. The expression or function of Wnt protein and/or FLT protein is preferably inhibited at least after the termination of the overexpression. The inhibition of the expression or function of Wnt protein and/or FLT protein prior to termination of the overexpression of these genes can cause the appearance of a declining trend for the number of CD41a-positive cells, i.e., the number of pre-multinucleated megakaryocyte cells. Because of this, from the standpoint of maintaining the number of pre-multinucleated megakaryocyte cells, the initiation of the inhibition of the expression or function of Wnt protein and/or FLT protein is more preferably after the termination of the overexpression of the indicated genes.

In another embodiment, the platelet production method according to the present invention contains a step for bringing megakaryocyte cells into contact with an aryl hydrocarbon receptor (AhR) antagonist. The contact between the AhR antagonist and cells can be performed in a culture medium.

In the case of use of "cells provided by the overexpression in cells less differentiated than megakaryocyte cells of at least 1 gene selected from the group consisting of oncogenes, polycomb genes, and apoptosis suppression genes followed by the termination of this overexpression", the period of time for overexpression is also not particularly limited and can be established as appropriate by the individual skilled in the art. The cells may be subcultured after overexpression, and the period of time after the final passage to the day of termination of overexpression is also not particularly limited, but can be exemplified by 1 day, 2 days, or 3 or more days.

Contact with the AhR antagonist is carried out with at least multinucleated megakaryocyte cells. When immortalized megakaryocyte cells are produced by the overexpression of an oncogene, polycomb gene, and apoptosis suppression gene in cells less differentiated than megakaryocyte cells followed by the termination of the overexpression and the development of multinucleation of the immortalized megakaryocyte cells, the AhR antagonist is preferably added to the culture medium after termination of the overexpression.

There are also no particular limitations on the period of time during which the megakaryocyte cells are cultured in the presence of the AhR antagonist. When the AhR antagonist is added to the culture medium after the aforementioned termination of overexpression, functional platelets are gradually released beginning about the third day after the addition of the AhR antagonist to the culture medium, and the number increases with the number of days of cultivation. When SR1 is added as the AhR antagonist, highly functional platelets in particular tend to be obtained when cultivation is carried out for 5 days, but the number of days of cultivation may be shorter or longer than this as long as functional platelets are obtained.

There are also no particular limitations on the period of time after termination of the overexpression of the aforementioned genes in the megakaryocyte cells until the addition of the AhR antagonist to the culture medium, but, for example, culture in the presence of the AhR antagonist may be started within 1 day, 2 days, or 3 days. One or more supplemental additions of the AhR antagonist may be made to the culture medium during the cultivation period.

In the platelet production method according to the present invention, contact with the megakaryocyte cells may be effected using the AhR antagonist in combination with a ROCK inhibitor. Platelets with a synergetically increased functionality can be obtained by effecting contact with megakaryocyte cells using the combination of an AhR antagonist with a ROCK inhibitor. The AhR antagonist and ROCK inhibitor may be added at the same time or either may be added first.

When immortalized megakaryocyte cells are produced by the overexpression of an oncogene, polycomb gene, and apoptosis suppression gene in cells less differentiated than megakaryocyte cells followed by the termination of the overexpression and the development of multinucleation of the immortalized megakaryocyte cells, the ROCK inhibitor is preferably added to the culture medium after the termination of the overexpression.

In yet another embodiment, the platelet production method according to the present invention includes a step for culturing megakaryocyte cells in which the expression or function of Wnt protein and/or FLT protein has been inhibited. This culture step may be carried out in the presence of an AhR antagonist. This culture step may also be carried out in the presence of a ROCK inhibitor. Moreover, this culture step may be carried out in the absence of feeder cells.

Common conditions may be used for the megakaryocyte cell culture conditions in all of the embodiments of the present invention. For example, the temperature may be approximately 35° C. to approximately 42° C., approximately 36° C. to approximately 40° C., or approximately 37° C. to approximately 39° C., while 5% $CO_2$ and/or 20% $O_2$ may be used. Static culture or shake culture may be used. There are also no particular limitations on the shaking rate in the case of shake culture, and, for example, 10 rpm to 200 rpm, 30 rpm to 150 rpm, and so forth can be used.

By culturing megakaryocyte cells as described in the preceding in the platelet production method according to the present invention, the megakaryocyte cells undergo maturation and platelets are produced from their cytoplasm. This maturation of the megakaryocyte cells refers to multinucleation of the megakaryocyte cells and the release of platelets.

The functionality of these platelets can be evaluated through measurements carried out in accordance with known methods. For example, the amount of activated platelets can be measured using the PAC-1 antibody, which is an antibody that binds specifically to the integrin $\alpha IIB\beta 3$ (glycoprotein IIb/IIIa, CD41a/CD61 complex) activation marker that is present on the membrane of activated platelets. The amount of activated platelets may also be measured using antibody to detect CD62b (P-selectin), which is likewise an activation marker for platelets. The amount of platelets can be measured, for example, using flow cytometry and carrying out gating with antibody to the activation-independent platelet markers CD61 or CD41, followed by detection of binding by PAC-1 antibody or anti-CD62P antibody to the platelets. These processes may be carried out in the presence of adenosine diphosphate (ADP).

Platelet functionality may also be evaluated by examining whether binding with fibrinogen in the presence of ADP occurs. The activation of integrin as required in the initial stage of thrombus formation is produced by the binding of fibrinogen by platelets. In addition, platelet functionality may also be evaluated by a method in which the thrombus formation capacity is visualized and observed in vivo, as shown in FIG. 6 in WO 2011/034073.

In this Description, expressions such as "highly functional platelets", "the platelet functionality is high", "functional platelets", and the like refer to a state that can be determined by the individual skilled in the art when, in comparison to platelets obtained by a conventional method, the functionality of the platelets measured by at least one of the aforementioned methods is significantly higher or, if not significantly higher, exhibits a high trend, or the functionality is the same as platelets isolated from the organism. Or, expressions such as "highly functional platelets", "the platelet functionality is high", and the like in this Description denote a platelet functionality, as measured by at least one of the aforementioned methods, that is at least 50%, at least 60%, at least 70%, at least 80%, or at least 90% that of natural platelets.

There are no particular limitations on the culture medium for the cultivation of the megakaryocyte cells, and known media suitable for the production of platelets from megakaryocyte cells, or media based thereon, may be used as appropriate. For example, a medium used for the culture of animal cells can be prepared to function as a basal medium. The basal medium can be exemplified by IMDM medium, medium 199 medium, Eagle's minimum essential medium (EMEM) medium, α-MEM medium, Dulbecco's modified Eagle's medium (DMEM) medium, Ham's F12 medium, RPMI 1640 medium, Fischer's medium, Neurobasal Medium (Life Technologies Corporation), and mixed media from the preceding.

The culture medium may contain serum or plasma or may be serum-free. As necessary, the medium may also contain one or more substances such as, for example, albumin, insulin, transferrin, selenium, fatty acid, trace elements, 2-mercaptoethanol, thiolglycerol, monothioglycerol (MTG), lipids, amino acids (for example, L-glutamine), ascorbic acid, heparin, nonessential amino acids, vitamins, growth factors, low molecular weight compounds, antibiotics, antioxidants, pyruvic acid, buffers, inorganic salts, and cytokines. The cytokines are proteins that promote blood cell differentiation and can be exemplified by vascular endothelial growth factor (VEGF), thrombopoietin (TPO), various TPO-like agents, stem cell factor (SCF), insulin-transferrin-selenite (ITS) supplement, and ADAM inhibitor. A preferred medium for the present invention is IMDM medium containing serum, insulin, transferrin, serine, thiolglycerol, ascorbic acid, and TPO. It may also contain SCF and may also contain heparin. The co-use of TPO and SCF is preferred. There are no particular limitations on the concentration of each, but the TPO can be approximately 10 ng/mL to approximately 200 ng/mL or approximately 50 ng/mL to approximately 100 ng/mL; the SCF can be approximately 10 ng/mL to approximately 200 ng/mL or approximately 50 ng/mL; and the heparin can be approximately 10 U/mL to approximately 100 U/mL or approximately 25 U/mL. A phorbol ester (for example, phorbol 12-myristate 13-acetate, PMA) may also be added.

Human serum is preferred when serum is used. In addition, human plasma and so forth may be used instead of serum. Using the method according to the present invention, platelets equivalent to those obtained using serum can be obtained even with the use of these components.

When a drug-responsive gene expression induction system, e.g., the Tet-on (registered trademark) or Tet-off (registered trademark) system, is used for overexpression of genes or the termination thereof, in the overexpression process the corresponding drug, for example, tetracycline or doxycycline, may be incorporated in the culture medium, and overexpression may be inhibited by its removal from the culture medium.

The step for culturing the megakaryocyte cells may be carried out in the present invention without feeder cells. As demonstrated in the following examples, the method according to the present invention can provide functional platelets even by culture in the absence of feeder cells.

In this Description, "feeder cells" refer to cells that are co-cultured with the target cells in order to adjust to the environment required for the culture of the cells (target cells) that are to be propagated or differentiated. Insofar as they are cells that can be distinguished from the target cells, the feeder cells may contain cells originating from the same species or may contain cells of heterologous origin. The feeder cells may be cells that have been treated with antibiotics or gamma radiation to be nonpropagating, or may be cells not thusly treated.

The present invention also encompasses platelets that have been produced by the method according to the present invention. As shown in the examples below, platelets produced by the method according to the present invention have a more developed open canalicular system than platelets produced in vitro by conventional methods and are recognized as morphologically close to natural platelets in that mitochondria can also be observed.

The method according to the present invention for producing a platelet formulation contains a step for producing platelets by culturing megakaryocyte cells using the method according to the present invention and recovering a platelet-rich fraction from the culture product; and a step for removing non-platelet blood cell components from the platelet fraction. The step for removing blood cell components can be carried out by removing the non-platelet blood cell components including megakaryocyte cells, using, for example, a leukocyte removal filter (for example, from Terumo Corporation or Asahi Kasei Medical Co., Ltd.). A more specific method for producing a platelet formulation is described in, for example, WO 2011/034073.

The method according to the present invention for producing a blood formulation contains a step for producing a platelet formulation using the method according to the present invention; and a step for mixing this platelet formulation with other components. Erythrocytes are an example of this other component.

In addition, other components that contribute to cell stabilization may be added to the platelet formulation and the blood formulation.

The present invention also encompasses a composition that contains multinucleated megakaryocyte cells, an AhR antagonist, and culture medium. This composition may be cryopreserved, or highly functional platelets may be obtained by culturing this composition as such. In the particular case of cryopreservation, the composition may contain, for example, a commercial cell cryopreservation reagent, glycerol, or DMSO, which protect the cells during freezing. Highly functional platelets can be obtained by thawing the frozen composition and culturing it.

The disclosures in all the patent documents and non-patent documents cited in this Description are incorporated in their entirety in this Description by reference.

Example 1 iPS Cells

An immortalized megakaryocyte line (MKCL SeV2) was produced in accordance with the method described by Nakamura et al., Cell Stem Cell, 2014 by the introduction of Bcl-xL, c-Myc, and Bmi1 into iPS cells (SeV2: cells produced, in accordance with the method of WO 2010/134526, by the introduction of c-MYC, OCT3/4, SOX2, and KLF4 into neonate human fibroblasts using a sendai virus vector). iPS cells (MK iPS #12) were produced from the immortalized megakaryocyte line (MKCL SeV2) according to the method described by Okita K et al., Stem Cells, 31(3):458-466, 2013. The obtained iPS cells (MK iPS #12) were cultured in accordance with the method described by Nakagawa M et al., Sci Rep. 8; 4:3594, 2014 using StemFit (registered trademark) AK03 (Ajinomoto) and laminin 511 (iMatrix 511 (Nippi)).

Homologous Recombination

Figure 1A:
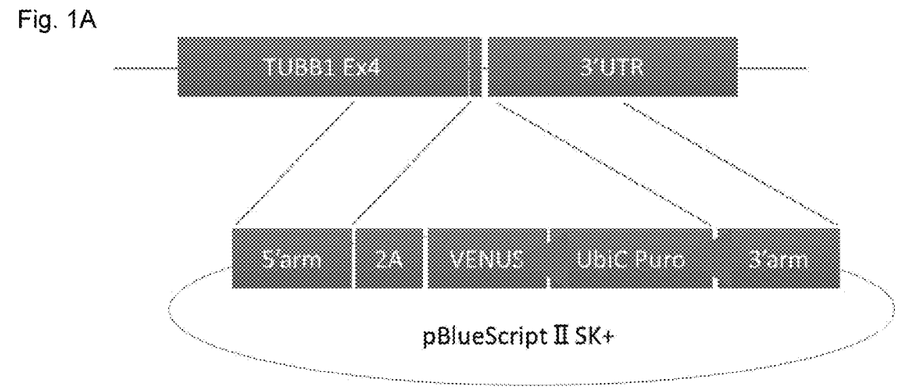
FIG. 1A is a structural diagram of pBlueScriptII SK+ (TUBB1–VENUS), which is a template vector.
Figure 1B:
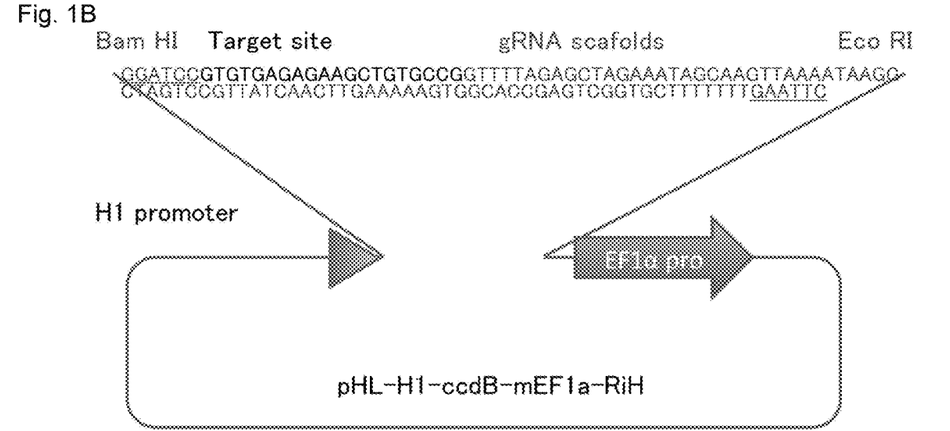
FIG. 1B is a structural diagram of pHL-H1-ccdB-mEF1a-RiH, which is a guide vector. The target sequence and neighboring sequences inserted in the guide vector are given as SEQ ID NO:1.

The iPS cells (MK iPS #12) were dissociated using TrypLE (registered trademark) Select, and $0.8 \times 10^6$ were mixed with 1.7 µg template vector (FIG. 1A), 1.7 guide vector (FIG. 1B), and 1.7 µg cas9 vector (pHL-EF1a-SphcCas9-iC-A, received from Dr. Hotta, Center for iPS Cell Research and Application, Kyoto University), and the vectors were introduced into the cells by electroporation using a Human Stem Cell Nucleofector (registered trademark) Kit 2 (Lonza) and Nucleofector. After electroporation, suspension was carried out in StemFit (registered trademark) AK03 followed by seeding to a laminin 511-coated 10-cm dish and culture under conditions of 37° C. and 5% $CO_2$. After 3 days, puromycin was added to the culture medium at 1 ng/mL and subculturing was performed. After 7 days, the colonies that had formed were picked up and DNA was extracted from each of the obtained colonies using a QIAamp DNA Mini Kit (QIAGEN), and homologous recombination was confirmed by genotyping PCR using primers (TUBB1 insert check Fw and Rv, 5-1 insert check Fw and 5-1.2 insert check Rv, and 3-1.2 insert check Fw and 3-2 insert check Rv; the sequences are given in Table 1). The homozygous homologous recombinant iPS cell line was expansion cultured and established as MK iPS#12-23.

TABLE 1

| primer name | sequence |
| --- | --- |
| TUBB1 insert check Fw | GATGCTTTACTGGTGCCCTT (SEQ ID NO: 2) |
| TUBB1 insert | AAGAGATGGCAGTGCTGCAT (SEQ ID NO: 3) |

TABLE 1-continued

| primer name | sequence |
| --- | --- |
| check Rv | |
| 5-1 insert check Fw | TGCTTTACTGGTGCCCTTCT (SEQ ID NO: 4) |
| 5-1.2 insert check Rv | AAGTCGTGCTGCTTCATGTG (SEQ ID NO: 5) |
| 3-1.2 insert check Fw | GCAACCTCCCCTTCTACGAG (SEQ ID NO: 6) |
| 3-2 insert check Rv | TCGGAGCATTTTCCCATTAC (SEQ ID NO: 7) |

The obtained MK iPS#12-23 was then mixed with 5 µg cre expression vector (pCXW-Cre-Puro, received from Dr. Hotta, Center for iPS Cell Research and Application, Kyoto University), and the vector was introduced into the cells by electroporation using a Human Stem Cell Nucleofector (registered trademark) Kit 2 (Lonza) and Nucleofector. After electroporation, suspension was carried out in StemFit (registered trademark) AK03 followed by seeding to a laminin 511-coated 10-cm dish and culture under conditions of 37° C. and 5% $CO_2$. After 9 days, multiple colonies were picked up and were divided in two: one half was cultured under the addition of puromycin at 1 ng/mL to the culture medium and the other half was stored. For stored cells deriving from the same colony for which cell death had been confirmed for the line, the removal of the puromycin resistance cassette was checked by genotyping PCR using primers (TUBB1 insert check Fw and Rv), and the resulting iPS cell line was expansion cultured to establish MK iPS#12-23 cre2.

Induction of Immortalized Megakaryocyte Cell Line

The induction of hematopoietic progenitor cells (HPC) was performed from the iPS cells (MK iPS#12-23 cre2) via iPS-sac. In more detail, the iPS cells were released from the culture dish using a cell scraper, and about one-twentieth of the cells were seeded as colony clusters onto mitomycin C (MMC)-treated C3H10T1/2 (available from Riken). The MMC-treated C3H10T1/2 was prepared by seeding $8\times10^5$ cells/dish to a 10-cm dish on the day prior to seeding with the iPS cells. After seeding, the culture was started (day 0) in Eagle's basal medium (EBM) supplemented with 20 ng/mL VEGF, in an environment of 5% $O_2$, 5% $CO_2$, and 37° C. Medium exchange with the same culture medium was performed at a frequency of twice per week.

The cells were physically released on day 14 using a cell scraper and the tip of a pipet, and cells of uniform size were recovered by passage through a 40-micrometer cell strainer.

On day 14, the cells were recovered and $1\times10^5$ cells/well were seeded to a 6-well dish on MMC-treated C3H10T1/2. The culture medium used was EBM supplemented with SCF at 50 ng/mL, TPO at 50 ng/mL, and doxycycline at 0.5 µg/mL. The cells were similarly recovered on day 17 and $1\times10^6$ cells/dish were seeded to a 10-cm dish on MMC-treated C3H10T1/2. The cells were recovered on day 23 and $1\times10^6$ cells/dish were seeded to a 10-cm dish to produce a reporter immortalized megakaryocyte cell line (MKCL#12-23 cre2).

Platelet Production

Figure 2A:
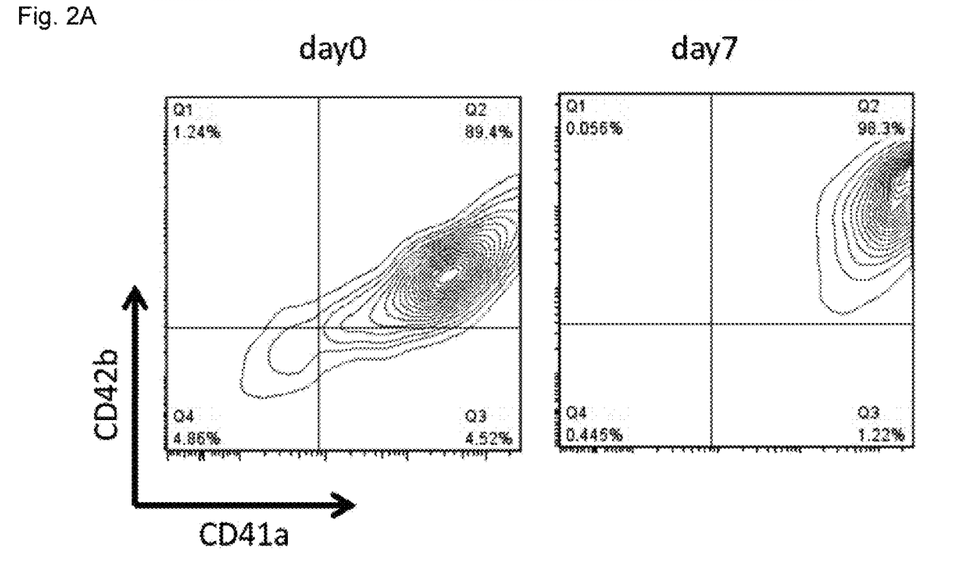
FIG. 2A gives the results of flow cytometric measurement of the distribution of cells expressing CD42b and CD41a for a reporter immortalized megakaryocyte line (MKCL #12-23 cre2).
Figure 2B:
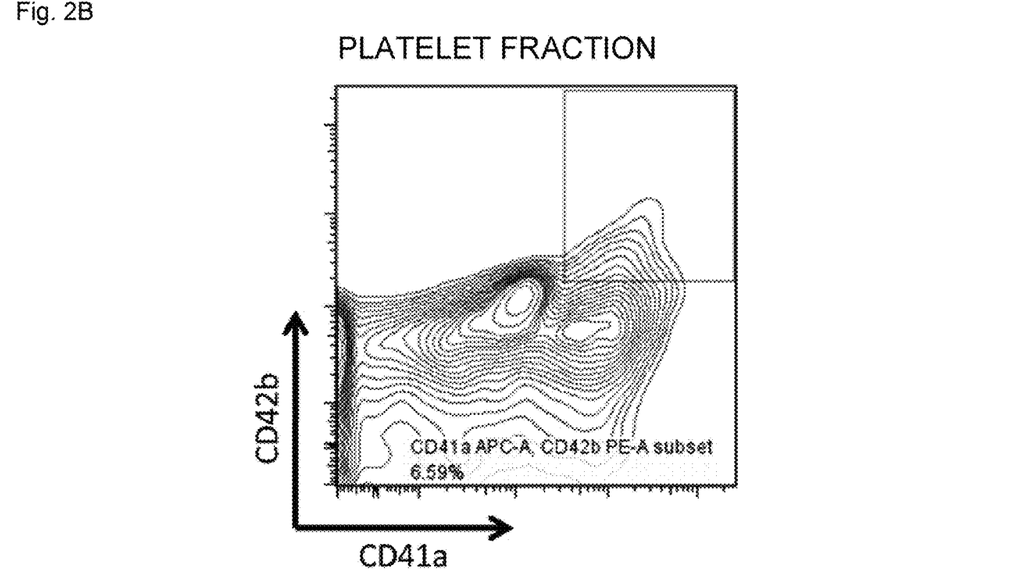
FIG. 2B gives the results of flow cytometric measurement of the distribution of cells expressing CD42b and CD41a for a fraction in which platelet production had been induced by culture on a differentiation medium that did not contain doxycycline.

The immortalized megakaryocyte line obtained by the method described above was cultured for 7 days on a differentiation medium supplemented with 0.75 µM Stem-Regenin1 (SR1) (Selleckchem), 10 µM Y-27632 (Wako), 50 ng/mL TPO (R & D), and 50 ng/mL SCF (R & D), and, after the cells had been suspended, the cells were recovered from the culture supernatant and were stained with anti-CD41 antibody and anti-CD42b antibody and FACS analysis was performed. FACS analysis was also similarly performed on the cells during the induction process. As a result, it was confirmed that, at the 7th day of culture, megakaryocytes positive for both CD41 and CD42b had been induced and platelets were produced from these megakaryocytes (FIG. 2).

Figure 3:
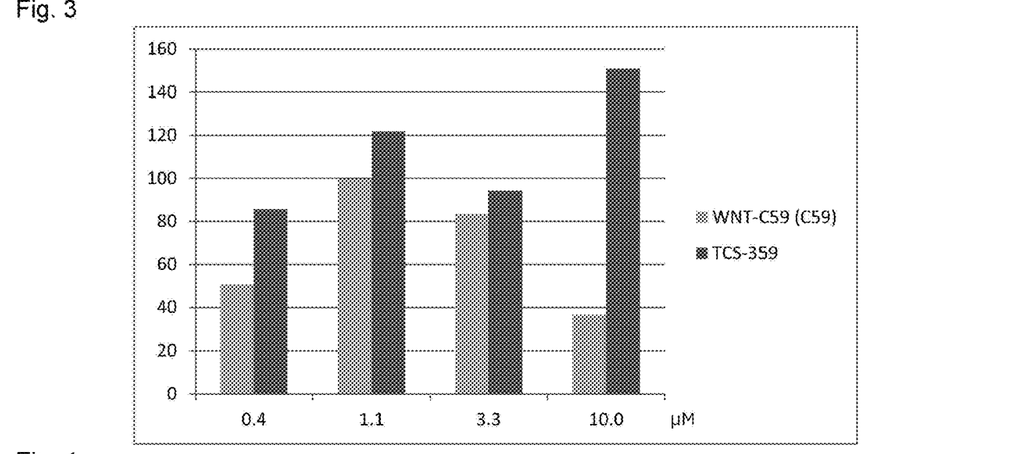
FIG. 3 gives the results for a comparison of the amount of platelet production by an immortalized megakaryocyte cell line cultured on media containing C59 or TCS-359 at a prescribed concentration.

Investigation of a Platelet Production-Promoting Effect Due to Wnt Inhibitor and FLT3 Inhibitor The platelet production-promoting effect of a Wnt inhibitor and FLT3 inhibitor was then investigated. The aforementioned reporter immortalized megakaryocyte cell line (MKCL#12-23 cre2) was cultured in a 96-well dish on a differentiation medium supplemented with the particular inhibitor at a prescribed concentration, 10 µM Y-27632, 50 ng/mL TPO, and 50 ng/mL SCF, or on a differentiation medium supplemented with 0.75 µM SR1, 10 µM Y-27632, 50 ng/mL TPO, and 50 ng/mL SCF (positive control), or on a differentiation medium supplemented with 0.1% DMSO, 10 µM Y-27632, 50 ng/mL TPO, and 50 ng/mL SCF (negative control). When the VENUS fluorescence intensity was measured on the cells on the 7th day of culture, the fluorescence intensity was increased for media to which the Wnt inhibitor or FLT3 inhibitor had been added. The results of calculation of the relative fluorescence intensity are given in FIG. 3, where the platelet count for use of the particular inhibitor was corrected with the platelet count for the positive control (made 100%) and the platelet count for the negative control (made 0%).

Figure 4:
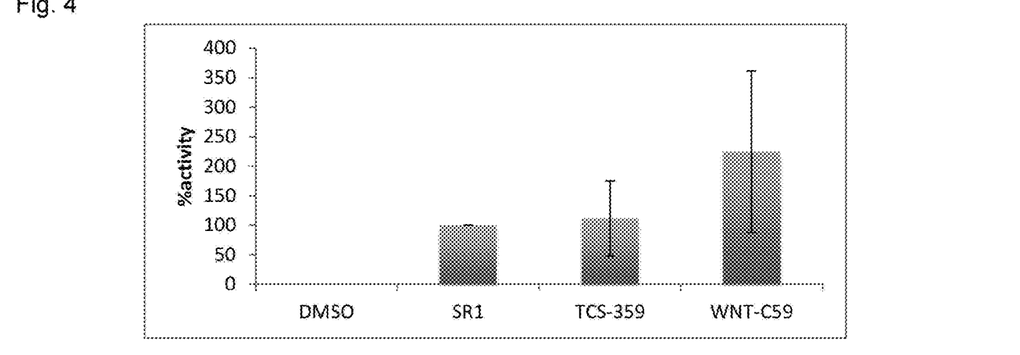
FIG. 4 gives the results of a comparison of the amount of platelet production for an immortalized megakaryocyte cell line cultured on media containing SR1, C59, or TCS-359.
Figure 5:
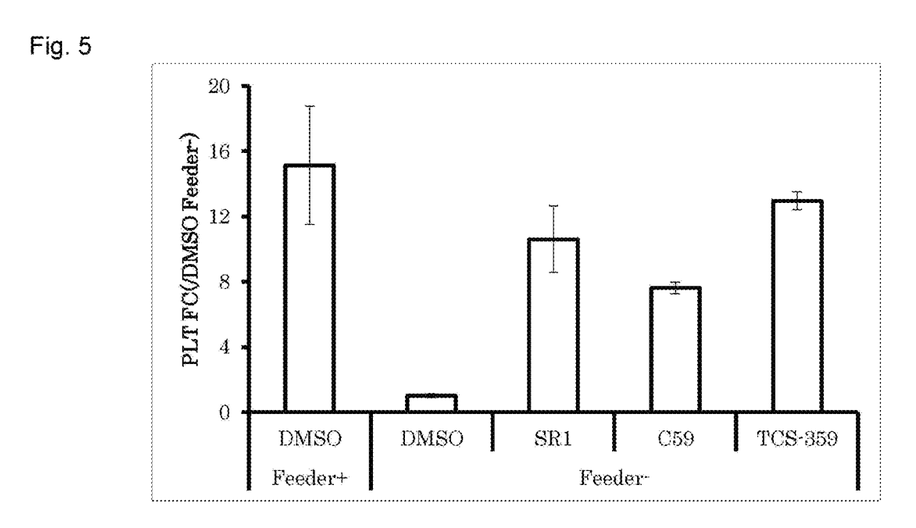
FIG. 5 gives the results of a comparison of the amount of platelet production, under conditions of nonuse of feeder cells, for an immortalized megakaryocyte cell line cultured on media containing SR1, C59, or TCS-359 in prescribed concentrations.

The platelet production-promoting effect of the Wnt inhibitor and FLT3 inhibitor was then investigated. MKCL SeV2, on which the aforementioned reporter immortalized megakaryocyte cell line (MKCL#12-23 cre2) was based, was cultured in a 6-well dish on a differentiation medium supplemented with the Wnt or FLT3 inhibitor, 10 µM Y-27632, 50 ng/mL TPO, and 50 ng/mL SCF, or on a differentiation medium supplemented with 0.75 µM SR1, 10 µM Y-27632, 50 ng/mL TPO, and 50 ng/mL SCF (positive control), or on a differentiation medium supplemented with 0.1% DMSO, 10 µM Y-27632, 50 ng/mL TPO, and 50 ng/mL SCF (negative control). On the 7th day of cultivation, the culture medium was suspended and the supernatant was recovered; staining with anti-CD41 antibody and anti-CD42b antibody was performed; and FACS analysis was carried out. The relative number of platelets was calculated with correction of the platelet count for use of the particular inhibitor with the platelet count for the positive control (made 100%) and the platelet count for the negative control (made 0%) (FIG. 4).

The preceding results suggest that a Wnt inhibitor and an FLT3 inhibitor are strong platelet inducers.

Effect of Wnt Inhibitor and FLT3 Inhibitor on Platelet Production Under the Condition of Nonuse of Feeder Cells iPS cells (TkDA3-4) were cultured and a colony was detached using a cell scraper and was cultured on a differentiation medium supplemented with 20 µg/mL VEGF. After 14 days, the cells were recovered using a cell scraper and 25 U/mL heparin, 10 µM Y-27632, 100 ng/mL TPO, and 50 ng/mL SCF were added. 0.1% DMSO, 0.75 µM SR1, 1 µM C59 (Calbiochem), or 3.3 µM FLT3 inhibitor (Santa Cruz Biotechnology) was also added to this culture medium and culture was carried out for 10 days. This was also carried out under the condition of the use of feeder cells as described above. The obtained cells were suspended and the supernatant was recovered; staining with anti-CD41 antibody and anti-CD42b antibody was performed; and FACS analysis was carried out (FIG. 4). As a result, it was confirmed that the compounds can substitute for a state, in which a feeder is not present, and that, under the condition of nonuse of a feeder, a Wnt inhibitor and FLT3 inhibitor have the same as or greater platelet production capacity than that of SR1.

What is claimed is:

1. A method of producing platelets comprising contacting megakaryocyte cells and/or progenitor cells thereof with one or more inhibitors selected from the group consisting of Wnt inhibitors and FLT inhibitors.

2. The method according to claim 1, wherein the Wnt inhibitors is C59.

3. The method according to claim 1, wherein the FLT inhibitors is an FLT3 inhibitor.

4. The method according to claim 1, further comprising contacting the megakaryocyte cells and/or progenitor cells with a ROCK inhibitor.

5. The method according to claim 1, wherein the megakaryocyte cells are immortalized megakaryocyte cells.

6. The cells according to claim 5, wherein the megakaryocyte cells are derived from pluripotent stem cells.

7. The method according to claim 6, wherein the pluripotent stem cells are induced pluripotent stem (iPS) cells.

8. The method according to claim 7, wherein the iPS cells are of human origin.

9. The method according to claim 3, wherein the FLT3 inhibitor is 2-[(3,4-dimethoxybenzoyl)amino]-4,5,6,7-tetrahydrobenzo[b]thiophene-3-carboxamide (TCS-359).

10. A platelet production promoter, which comprises a Wnt inhibitor which is C59, a FLT3 inhibitor which is 2-[(3,4-dimethoxybenzoyl)amino]-4,5,6,7-tetrahydrobenzo[b]thiophene-3-carboxamide (TCS-359), and a ROCK inhibitor.

11. A method of producing platelets comprising contacting megakaryocyte cells and/or progenitor cells thereof with the platelet production promoter according to claim 10.

12. The method according to claim 11, wherein the megakaryocyte cells are immortalized megakaryocyte cells.

13. The cells according to claim 12, wherein the megakaryocyte cells are derived from pluripotent stem cells.

14. The method according to claim 13, wherein the pluripotent stem cells are induced pluripotent stem (iPS) cells.

15. The method according to claim 14, wherein the iPS cells are of human origin.

* * * * *

SEQUENCE LISTING

<160> NUMBER OF SEQ ID NOS: 7

<210> SEQ ID NO 1
<211> LENGTH: 115
<212> TYPE: DNA
<213> ORGANISM: Artificial Sequence
<220> FEATURE:
<223> OTHER INFORMATION: Target vector

<400> SEQUENCE: 1
ggatccgtgt gagagaagct gtgccggttt tagagctaga aatagcaagt taaaataagg    60
ctagtccgtt atcaacttga aaaagtggca ccgagtcggt gcttttttttg aattc       115

<210> SEQ ID NO 2
<211> LENGTH: 20
<212> TYPE: DNA
<213> ORGANISM: Artificial Sequence
<220> FEATURE:
<223> OTHER INFORMATION: TUBB1 insert check Fw

<400> SEQUENCE: 2
gatgctttac tggtgcccttt                                              20

<210> SEQ ID NO 3
<211> LENGTH: 20
<212> TYPE: DNA
<213> ORGANISM: Artificial Sequence
<220> FEATURE:
<223> OTHER INFORMATION: TUBB1 insert check Rv

<400> SEQUENCE: 3
aagagatggc agtgctgcat                                               20

<210> SEQ ID NO 4
<211> LENGTH: 20
<212> TYPE: DNA
<213> ORGANISM: Artificial Sequence
<220> FEATURE:
<223> OTHER INFORMATION: 5-1 insert check Fw

<400> SEQUENCE: 4
tgctttactg gtgcccttct                                               20

<210> SEQ ID NO 5
<211> LENGTH: 20
<212> TYPE: DNA
<213> ORGANISM: Artificial Sequence
<220> FEATURE:
<223> OTHER INFORMATION: 5-1.2 insert check Rv

<400> SEQUENCE: 5
aagtcgtgct gcttcatgtg                                               20

<210> SEQ ID NO 6
<211> LENGTH: 20
<212> TYPE: DNA
<213> ORGANISM: Artificial Sequence
<220> FEATURE:
<223> OTHER INFORMATION: 3-1.2 insert check Fw

<400> SEQUENCE: 6
gcaacctccc cttctacgag                                               20

<210> SEQ ID NO 7
<211> LENGTH: 20

```
<212> TYPE: DNA
<213> ORGANISM: Artificial Sequence
<220> FEATURE:
<223> OTHER INFORMATION: 3-2 insert check Rv

<400> SEQUENCE: 7
tcggagcatt ttcccattac                                              20
```